United States Patent
Jacobs

(10) Patent No.: US 12,383,610 B2
(45) Date of Patent: Aug. 12, 2025

(54) VACCINE FOR PROTECTION AGAINST *Streptococcus suis* SEROTYPE 9, SEQUENCE TYPE 16

(71) Applicant: Intervet Inc., Madison, NJ (US)

(72) Inventor: Antonius Arnoldus Christiaan Jacobs, Kessel (NL)

(73) Assignee: Intervet Inc., Rahway, NJ (US)

( * ) Notice: Subject to any disclaimer, the term of this patent is extended or adjusted under 35 U.S.C. 154(b) by 102 days.

(21) Appl. No.: 17/909,917

(22) PCT Filed: Mar. 12, 2021

(86) PCT No.: PCT/EP2021/056285
§ 371 (c)(1),
(2) Date: Sep. 7, 2022

(87) PCT Pub. No.: WO2021/185680
PCT Pub. Date: Sep. 23, 2021

(65) Prior Publication Data
US 2024/0197851 A1    Jun. 20, 2024

(30) Foreign Application Priority Data

Mar. 14, 2020  (EP) .................................... 20163206

(51) Int. Cl.
| | | |
|---|---|---|
| *A61K 39/09* | (2006.01) | |
| *A61K 39/00* | (2006.01) | |
| *A61P 31/04* | (2006.01) | |
| *A61P 37/04* | (2006.01) | |

(52) U.S. Cl.
CPC ............ *A61K 39/092* (2013.01); *A61P 31/04* (2018.01); *A61P 37/04* (2018.01); *A61K 2039/552* (2013.01); *A61K 2039/70* (2013.01)

(58) Field of Classification Search
None
See application file for complete search history.

(56) References Cited

FOREIGN PATENT DOCUMENTS

| | | |
|---|---|---|
| WO | 2015181356 A1 | 12/2015 |
| WO | 2019115741 A1 | 6/2019 |
| WO | 2019115743 A1 | 6/2019 |
| WO | 2020094762 A1 | 5/2020 |

OTHER PUBLICATIONS

Buttner, Nadine et al., *Streptococcus suis* serotype 9 bacterin immunogenicity and protective efficacy, Veterinary Immunology and Immunopathology, 2012, 191-200, 146(3).
Haesebrouck, Freddy et al., Efficacy of vaccines against bacterial diseases in swine: What can we expect?, Veterinary Microbiology, 2004, 255-268, 100(3-4).
Hsueh, Kai-Jan et al., Immunization with Streptococcus suis bacterin plus recombinant Sao protein in sows conveys passive immunity to their piglets, BMC Veterinary Research, 2016, 1-9, 13.
King, Samantha J et al, Development of a Multilocus Sequence Typing Scheme for the Pig Pathogen *Streptococcus suis*: Identification of Virulent Clones and Potential Capsular Serotype Exchange, Journal of Clinical Microbiology,, 2992, p. 3671-3680, vol. 40, No. 10.
Reickmann et al, Vaccination with the immunoglobulin M-degrading enzyme of *Streptococcus suis*, Idessuis, leads to protection against a highly virulent serotype 9 strain, Vaccine: X 3, 2019, pp. 1, 100046, ELSEVIER.
Seele, J et al, The immunoglobulin M-degrading enzyme of *Streptococcus suis*, IdeSsuis, is a highly protective antigen against serotype 2, Vaccine, 2015, pp. 2207-2212, vol. 33 No. 19, Elsevier, EP.
Segura, M., *Streptococcus suis* vaccines: candidate antigens and progress, Expert Review of Vaccines, 2015, pp. 1587-1608, 14(12).
Harkevich D.A., Pharmacology: Textbook, Ways of Drug Administration. Suction, M.: GEOTAR-Media, 10th Edition, 908, 42, 2010.
Kharkevich, D.A., Pharmacology, Moscow: GEOTAR-Media, Textbook for HS, 10th Ed., 73-74, 2010.
Svistunov, A.A., et al., Pharmacology: Textbook, M.: Laboratory of Knowledge, N/A, 55-56, 2017.

*Primary Examiner* — Brian Gangle
(74) *Attorney, Agent, or Firm* — Susanna C. Benn

(57) ABSTRACT

The present invention pertains to a vaccine comprising in combination an IgM protease antigen of *Streptococcus suis* and a *Streptococcus suis* bacterin of serotype (9), sequence type (16), for use in a method for protecting pigs against a pathogenic infection with *Streptococcus suis* serotype (9), sequence type (16).

14 Claims, No Drawings

VACCINE FOR PROTECTION AGAINST *Streptococcus suis* SEROTYPE 9, SEQUENCE TYPE 16

CROSS-REFERENCE TO RELATED APPLICATIONS

This application is a National Stage application of International Patent Application No. PCT/EP2021/056285, filed Mar. 12, 2021, which claims priority to European Patent Application No. EP 20163206.4, filed Mar. 14, 2020.

GENERAL FIELD OF THE INVENTION

The invention pertains to the protection of pigs against a pathogenic infection with *Streptococcus suis* bacteria of serotype 9, sequence type 16.

BACKGROUND OF THE INVENTION

*Streptococcus suis* (*S. suis*) is one of the principal etiologic agents of contagious bacterial disease in pigs. The pathogen can cause a variety of clinical syndromes including meningitis, arthritis, pericarditis, polyserositis, septicaemia, pneumonia and sudden death. *S. suis* is a gram-positive facultatively anaerobic coccus, originally defined as Lancefield groups R, S, R/S or T. Later, a new typing system based on the type-specific capsular polysaccharide antigens located in the cell wall was proposed. This led to a system comprising 35 serotypes (Rasmussen and Andresen, 1998, "16S rDNA sequence variations of some *Streptococcus suis* serotypes", Int. J. Syst. Bacteriol. 48, 1063-1065) of which serotypes 2, 9, 1, 7 and ½ are the most prevalent. However, it is recognised that the capsular serotype is a poor marker of virulence. Therefor an alternative system to helping understand the epidemiology of *S. suis* infection and the biological relevance of the serotyping approach was developed, i.e. the so called multilocus sequence typing (MLST), as described by King et al. in the Journal of Clinical Microbiology, October 2002, p. 3671-3680 (*Development of a Multilocus Sequence Typing Scheme for the pig pathogen Streptococcus suis: Identification of virulent clones and potential capsular serotype exchange*). In that study 92 sequence types were identified, of which ST complexes ST1, ST27 and ST87, each containing multiple sequence types, dominate the population. See also the *Streptococcus suis* MLST website (https://pubmlst.org/ssuis/) sited at the University of Oxford (Jolley et al. Wellcome Open Res 2018, 3:124 (site funded by the Wellcome Trust), which refers to the King et al. paper and allows for easy identification of the sequence type for any *Streptococcus suis* strain.

Control of *Streptococcus suis* in pig herd appears to be difficult. *Streptococcus suis* is a commensal and opportunistic pathogen of swine. Apparently, the immune system is not triggered in each and every occasion of an infection. Next to this, *Streptococcus suis* is a well-encapsulated pathogen and uses an arsenal of virulence factors to evade the host immune system. Together, these characteristics have challenged the development of efficacious vaccines to fight this important pathogen. Recently, an overview article has been published regarding vaccines against *Streptococcus suis* (Mariela Segura: "*Streptococcus suis* vaccines: candidate antigens and progress, in *Expert Review of Vaccines*, Volume 14, 2015, Issue 12, pages 1587-1608). In this review, clinical field information and experimental data have been compiled and compared to give an overview of the current status of vaccine development against *Streptococcus suis* as outlined here below.

Current commercial vaccines are mainly whole-cell bacterins. However, field reports describe difficulty in disease control and management, and specially "vaccine failures" when using bacterin vaccines are common. Carrier pigs are the primary source of infection, and both vertical and horizontal transmission are involved in spread of the disease within a herd. Mixing of carrier animals with susceptible animals under stressful conditions such as weaning and transportation usually results in clinical disease. Early medicated weaning and segregated early weaning practices do not eliminate *Streptococcus suis* infection. Therefore, effective control measures to prevent disease will hinge on prophylactic/methyllactic procedures (where allowed) and on vaccination. Currently, field immunization efforts have focused on the use of commercial or autogenous bacterins. These vaccine strategies have been applied to either piglets or sows. From weaning and onwards piglets are more susceptible to *Streptococcus suis* infections due to the stresses associated with weaning and also, the common subsequent transport. Therefore, prepartum immunization in sows is often used to try and convey passive immunity to piglets and provide protection against *Streptococcus suis* under these stressful circumstances early in life. Moreover, sow vaccination is less costly and labor intensive, thus representing an economical alternative to piglet vaccination. Yet, available results seem to indicate that sow vaccination with bacterins is also a matter of controversy. In many cases vaccinated sows, even when vaccinated twice before parturition, respond poorly or not at all to vaccination which results in low maternal immunity transferred to the litters. And even if maternal immunity is transferred at a sufficient level, in many cases the maternal antibodies are too low to provide protection in the most critical period of 4-7 weeks of age.

In piglets, autogenous bacterins are frequently used in the field, especially in Europe. They are prepared from the virulent strain isolated on the farm with clinical problems and applied to the same farm. One of the disadvantages of autogenous bacterins is that vaccine safety data are lacking and severe adverse reactions may occur. Sampling errors (due to using only one or two pigs or samples) may result in failure to identify a strain or serotype associated with a recent outbreak. This failure may be especially problematic in endemic herds. Finally, the most important dilemma of autogenous bacterins is that their actual efficacy has been poorly studied. As application of autogenous vaccines is empirical, it is not surprising that results obtained with these vaccines are inconsistent and often disappointing.

Other experimental vaccines are also described in the art. Kai-Jen Hsueh et al. show ("Immunization with *Streptococcus suis* bacterin plus recombinant Sao protein in sows conveys passive immunity to their piglets", in: *BMC Veterinary Research, BMC series—open, inclusive and trusted*, 13:15, 7 Jan. 2017) that a bacterin plus subunit might be a basis for successful vaccination of sows to confer protective immunity to their piglets.

Live attenuated vaccines have also been contemplated in the art. Non encapsulated isogenic mutants of *Streptococcus suis* serotype 2 have been clearly shown to be avirulent. Yet, a live vaccine formulation based on a non encapsulated serotype 2 mutant induced only partial protection against mortality and failed to prevent the development of clinical signs in pigs challenged with the wildtype strain (Wisselink H J, Stockhofe-Zurwieden N, Hilgers L A, et al. "Assessment of protective efficacy of live and killed vaccines based on a non-encapsulated mutant of *Streptococcus suis* serotype 2." in: *Vet Microbiol.* 2002, 84:155-168.)

In the last couple of years, an extensive list of antigenic or immunogenic *Streptococcus suis* molecules has been reported, and most of these have been discovered through immuno proteomics using either convalescent sera from infected pigs or humans and/or laboratory-produced immune sera. WO2015/181356 (IDT Biologika GmbH) has shown that IgM protease antigens (either the whole protein or the highly conserved Mac-1 domain representing only about 35% of the full protein) can elicit a protective immune response in piglets in a vaccination scheme of administering two doses of the IgM protease antigen, optionally in combination with a prime vaccination containing a bacterin. It is noted that WO2017/005913 (Intervacc AB) also describes the use of an IgM protease antigen (in particular, an IgM protease polypeptide fused to a nucleotidase). However, only the property of being able to elicit a seroresponse has been shown. A protective effect for an IgM protease antigen is not shown in this international patent application.

Recently WO 2019/115741 (assigned to the current applicant) has been published. In this patent application it is shown that the IgM protease antigen is effective to protect against a pathogenic infection with *Streptococcus suis* of serotype 9. However, the protection is not very high, and appears to be at the level obtainable with a common bacterin vaccine, i.e. a reduction of about 50% in deaths and positive blood isolation in an artificial challenge experiment (not excluding that in practice protection will be at a higher level). At first glance, this somewhat disappointing protection seems to be in conflict with the high level of protection obtained with an IgM protease antigen against an infection with *Streptococcus suis* of serotype 9 as reported by Rieckmann et al. in Vaccine, 3 (2019) 100046 ("Vaccination with the immunoglobulin M-degrading enzyme of *Streptococcus suis*, IdeSsuis, leads to protection against a highly virulent serotype 9 strain"), also in an artificial challenge experiment.

Object of the Invention

It is an object of the invention to find a composition and treatment that is more effective in protection of pigs against *Streptococcus suis* of various serotypes, including serotype 9.

SUMMARY OF THE INVENTION

It is known that with an IgM protease antigen a very good protection can be obtained across various serotypes, including serotype 1, 2, 9 and 14. In this respect the results as reported in WO 2019/115741 with regard to the level of protection obtainable against serotype 9 seem to be in conflict with the results as reported in Rieckmann. However, on close examination, it appears that in the Rieckmann study, a *Streptococcus suis* strain of Sequence Type 94 is used. In WO 2019/115741, although not indicated, a *Streptococcus suis* strain of Sequence Type 16 is used. This was found later by typing the used challenge strain according to the multilocus sequence typing as described by King et al (see above). Apparently, against the later type (*S. suis* of serotype 9, sequence type 16) the IgM protease antigen provides protection at a substantially lower level. The reason for this is not clear, but very disadvantageous since in many countries, especially European countries such as The Netherlands, *Streptococcus suis* of sequence type 16 is the most prevalent (up to about 95%) pathogenic type of *Streptococcus suis* serotype 9 bacteria (Willemse et al. Scientific Reports, 2019, 9: 15429, "Clonal expansion of a virulent *Streptococcus suis* serotype 9 lineage distinguishable from carriage subpopulations). Thus, although an IgM protease may give rise to broad protection across serotypes, it was found that there is a gap in effective protection in particular with respect to *Streptococcus suis* serotype 9, sequence type 16.

After finding this gap, it was found that this gap can be closed by using in combination an IgM protease antigen of *Streptococcus suis* and a *Streptococcus suis* bacterin of serotype 9, sequence type 16, to protect pigs against a pathogenic infection with *Streptococcus suis* serotype 9, sequence type 16, and that a level of protection can be arrived at that is improved over a level obtainable with the IgM protease only (in particular to arrive at a death figure and blood isolation score well below 50% with respect to unvaccinated control animals in an artificial challenge model). This is highly unexpected since the two antigens overlap (a bacterin inherently also comprises all of its subunits) and each antigen as such provides less protection, whereas in combination they provide protection to a level obtainable with the most effective known vaccine against other *S. suis* strains, i.e. protection at a level which an IgM protease antigen based vaccine is able to provide against various different (non serotype 9, sequence type 16) *Streptococcus suis* strains. It is thus shown that the antigens in combination provide a better than expected protection. It has been shown that this effect comes about by the concurrent administration of the two antigens, whether as separate single vaccines (via two separate administrations) or when formulated in one (unitary) vaccine for one single administration to administer both antigens in one go.

Said otherwise, the invention also pertains to an IgM protease antigen of *Streptococcus suis*, for use in a method wherein the IgM protease is administered concurrently with a *Streptococcus suis* bacterin of serotype 9, sequence type 16 for protecting pigs against a pathogenic infection with *Streptococcus suis* serotype 9, sequence type 16. Or, in the alternative, the invention pertains to a *Streptococcus suis* bacterin of serotype 9, sequence type 16, for use in a method wherein the said bacterin is administered concurrently with an IgM protease antigen of *Streptococcus suis* for protecting pigs against a pathogenic infection with *Streptococcus suis* serotype 9, sequence type 16. The said concurrent administration can be in the form of two separate administrations of two separate formulations (one containing the IgM protease antigen and the other containing the bacterin) or one administration of one unitary combination vaccine comprising both antigens in one single formulation.

With this invention the gap in protection against *Streptococcus suis* bacteria, can be closed. The invention enables not only to arrive at the best possible protection against *Streptococcus suis* of serotype 9 including sequence type 16 as an important representative, but also, to arrive at a method to arrive at a very broad protection across all serotypes. The IgM protease antigen has been shown namely to provide broad protection across serotypes and that protection will be present inherently when using the current combination of antigens.

The invention also pertains to a kit-of-parts comprising in combination an IgM protease antigen of *Streptococcus suis*, a *Streptococcus suis* bacterin serotype 9, sequence type 16, and a pharmaceutically acceptable carrier.

The invention also pertains to a unitary vaccine composition comprising in combination an IgM protease antigen of

*Streptococcus suis*, a *Streptococcus suis* bacterin of serotype 9 sequence type 16 and a pharmaceutically acceptable carrier.

The invention also pertains to the use of an IgM protease antigen of *Streptococcus suis* and a *Streptococcus suis* bacterin serotype 9, sequence type 16 for the manufacture of a vaccine for protecting pigs against a pathogenic infection with *Streptococcus suis* of serotype 9, sequence type 16.

Lastly, the invention pertains to a method for protecting pigs against a pathogenic infection with *Streptococcus suis* of serotype 9, sequence type 16, by administering to the pigs an IgM protease antigen of *Streptococcus suis* and a *Streptococcus suis* bacterin of serotype 9, sequence type 16.

Definitions

An IgM protease antigen of *Streptococcus suis* is an enzyme that specifically degrades porcine IgM (and not porcine IgG or porcine IgA; Seele at al, in *Journal of Bacteriology*, 2013, 195 930-940; and in Vaccine 33:2207-2212; 5 May 2015), a protein denoted as IdeSsuis, or an immunogenic part thereof (typically having a length of at least about 30-35% of the full length enzyme). The whole enzyme has a weight of about 100-125 kDa, corresponding to about 1000-1150 amino acids, the size depending on the serotype of *S. suis*. In WO 2015/181356 several sequences that represent an IgM protease antigen of *Streptococcus suis* are given, viz. SEQ ID NO:1, SEQ ID NO:2, SEQ ID NO:6, SEQ ID NO:7 and SEQ ID NO:5, the latter being an immunogenic part of the full length enzyme (denoted as the Mac-1 domain, i.e. amino acids 80-414 of SEQ ID NO:7). Other examples of immunogenic parts of the full length enzyme are given in WO2017/005913. In particular the IgM protease may be the protease according to SEQ ID NO:1 of WO2015/1818356 or a protein having at least 90%, or even 91, 92, 93, 94, 95, 96, 97, 98, 99% up to 100% sequence identity in the overlapping regions. The amino acid sequence identity may be established with the BLAST program using the blastp algorithm with default parameters. It is expected that the IgM proteases of *Streptococcus suis* of various serotypes have a sequence identity higher than 90%, in particular expected to be 91, 92, 93, 94, 95, 96, 97, 98, 99% up to 100%. An artificial protein, for example made to optimize yield in a recombinant production system of the antigen, may lead to a lower amino acid sequence identity such as 85%, 80%, 75%, 70% or even 60% compared with the whole enzyme, while maintaining the required immunogenic function, and is understood to be an IgM protease antigen of *Streptococcus suis* in the sense of the present invention.

A vaccine is a constitution suitable for application to a subject, comprising one or more antigens in an immunologically effective amount (i.e. capable of stimulating the immune system of the target subject sufficiently to at least reduce the negative effects of a challenge of the wild-type micro-organisms), typically combined with a pharmaceutically acceptable carrier, which upon administration to the subject induces an immune response for treating an infection, i.e. aiding in preventing, ameliorating or curing the infection or any disease or disorder arising from that infection.

Protection against a pathogenic infection with a microorganism is the same as arriving at protective immunity, i.e. aiding in preventing, ameliorating or curing the pathogenic infection with that micro-organism or a disorder arising from that infection, for example to prevent or reduce of the actual infection or one or more clinical signs resulting from the pathogenic infection with the pathogen.

A bacterin is a suspension of killed bacteria for use as a vaccine.

A combination of antigens is a joined use of these (individually distinct) antigens in one vaccination strategy, either by joining the distinct antigens in one vaccine formulation or by using separate antigen formulations for concurrent administration of the separate formulations.

A unitary vaccine composition is a vaccine that forms a single entity, such as a single liquid comprising all ingredients of the vaccine combined in one single mixture.

A pharmaceutically acceptable carrier is a biocompatible medium, viz. a medium that after administration does not induce significant adverse reactions in the treated subject, capable of presenting the antigen to the immune system of the subject after administration of the composition comprising the carrier. Such a pharmaceutically acceptable carrier may for example be a liquid containing water and/or any other biocompatible solvent or a solid carrier such as commonly used to obtain freeze-dried vaccines (based on sugars and/or proteins), optionally comprising immunostimulating agents (adjuvants). Optionally other substances such as stabilisers, viscosity modifiers or other components are added depending on the intended use or required properties of the corresponding vaccine.

Further Embodiments of the Invention

Although the two antigens of the combination of present invention may be administered separately, in a further embodiment the IgM protease antigen of *Streptococcus suis* and the *Streptococcus suis* bacterin are comprised in a single composition for administration to the pigs. It was found that the combined effect is improved when both antigens are present in single composition that can be administered with a single administration.

In another embodiment, the combination for use according to the invention comprises an IgM protease antigen of *Streptococcus suis* serotype 2. Although it is known that the IgM protease is able to induce cross protection between serotypes 2 and 9 (see WO 2019/115741 for the IgM protease), it was found that the combination of an IgM protease of serotype 2 and a bacterin of serotype 9 is advantageously useful for arriving at protection against *Streptococcus suis* serotype 9, sequence type 16. Concommittant advantage is that the combination provides wide cross-protection among various serotypes, such as 2, 9, 7 and 14 as known for the IgM protease antigen of serotype 2. Correspondingly, also for the kit-of-parts, the unitary vaccine, the use of the antigens for manufacturing a vaccine and the method of treatment, all identified here above in the Summary of the Invention section as other embodiments of the same inventive concept, the antigens are advantageously selected from a serotype 2 IgM protease.

In yet another embodiment, the antigens are administered to the pigs at an age of at most 35 days. As indicated here above, *Streptococcus suis* is a commensal and opportunistic pathogen of swine. In particular under stress, the bacterium may elicit a pathogenic infection and induce disease. Under modern pig producing conditions, major stress is induced on or after the pigs reach an age of 35 days, for example induced by the weaning of piglets (3-4 weeks) and transport of young piglets soon thereafter. In order to be protected against a pathogenic infection with *Streptococcus suis*, the pigs thus need to receive their vaccine at a very young age, typically before they reach the age of 28 days. It was found that by using the combination of antigens according to the present invention in pigs at an age of at most 35 days, i.e. any age of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 days, adequate protection may be obtained. As is known form the art, a positive immune response against an IgM protease antigen (WO2017/005913) and bacterins (as applied commonly in piglets before weaning) can be obtained in young pigs from the day of birth and onwards. This means that by the present showing of actual protection in 3-5 week old pigs, it is understood that protection can be obtained even at a younger age.

In another embodiment the antigens are administered before an age at which the pigs are weaned. In other words, the antigen is administered before the piglets are actually weaned (typically at an age of 3-4 weeks). It has been shown that by administering the antigens at this early age, protection can be obtained against a pathogenic infection with *Streptococcus suis* serotype 9, sequence type 16, induced by stress within a short window of 2-3 weeks right after weaning. It is acknowledged that WO2015/181356 shows successful vaccination using an IgM protease as antigen. However, the vaccine was used in piglets having an age of 5-7 weeks and receiving a challenge infection at an age of 9 weeks, thus well after the risk period (i.e. the period of peak incidence of pathogenic *Streptococcus suis* infections) of 2-3 weeks after weaning/transport, i.e. 5-7 weeks of age. So without any proof of effectiveness under practical circumstances (i.e. challenge infection in the window 2-3 weeks after weaning and transportation stress) it is still questionable whether the vaccine strategy as described in WO 2015/181356 is effective under practical circumstances.

All of the above embodiments are correspondingly also embodiments of the other representatives of the invention as defined here above in the Summary of the Invention section, i.e. the respective use of the IgM protease antigen and the bacterin, the kit-of-parts, the unitary vaccine, the use for manufacturing and the method of protecting.

The invention will now be further explained based on the following example.

EXAMPLE

The aim of this study was to test whether the combined administration of an IgM protease antigen and a bacterin of serotype 9, sequence type 16, in this example an IgM protease antigen of *Streptococcus suis* serotype 2, is able to provide protection against a challenge with *Streptococcus suis* of serotype 9, sequence type 16 such that in the artificial challenge model as used in WO2019/115741 the level of protection is better than obtainable with a known IgM protease or commonly used bacterin alone (i.e. better than about 50% reduction in death figure and blood re-isolation after challenge).

The antigens used are antigens as described in the prior art. The IgM protease corresponds to the antigen as described in WO2019/115741, namely the *E. coli* expressed rIdeSsuis IgM protease antigen as described by Seele et al in Vaccine 33:2207-2212; 5 May 2015, par. 2.2, but without the His-tag. The bacterin is a regular chlorocresol killed *Streptococcus suis* bacterium.

Study Design

The study design was the same as in WO2019/115741, albeit that in the current set-up, the dose of the IgM protease was substantially lower (80 μg vs 230 μg). Also, vaccination and challenge took place two weeks earlier, to be more in line with the critical period for a pathogenic *Streptococcus suis* infection. This means that in the present set-up, if anything, it will be more difficult to arrive at the same vaccine efficacy as obtainable in the study as described in WO2019/115741.

In the study thirty-six 3-week-old piglets were used. The piglets were allotted to three groups (evenly distributed over the different litters) of 12 piglets each. Groups 1 and 2 were vaccinated twice intramuscularly at 3 and 5 weeks of age with each of the two different combination vaccines. Group 1 was vaccinated with a unitary vaccine composition (2 ml per dose) comprising in combination the IgM protease antigen of *Streptococcus suis* serotype 2 (at 80 μg/dose) and a *Streptococcus suis* bacterin of serotype 9, ST16 (at $2\times10^9$ cells/dose) in oil-in-water adjuvant. Group 2 was vaccinated at each occasion with two separate vaccines, one containing the IgM protease (same dose) at the right side of the neck, and one containing the bacterin (at the same dose) on the left side of the neck, both formulated in the same oil-in-water adjuvant as used for Group 1. Group 3 remained unvaccinated. At 7 weeks of age the pigs were challenged intratracheally with a virulent culture of *S. suis* serotype 9, sequence type ST16.

After challenge the pigs were daily observed for clinical signs of *S. suis* infection such as depression, locomotory problems and/or neurological signs for 11 days and scored using a regular scoring system going from 0 (no signs) to 3 for severe cases. Animals reaching the humane endpoint were euthanized. Just before vaccination and challenge, serum blood was collected for antibody determination. At regular times before and after challenge heparin blood was collected for re-isolation of challenge strain.

Results

None of the vaccines induced any unacceptable site or systemic reactions and thus could be considered safe. Before challenge one animal in Group 1 became cripple and was treated accordingly. The animal did not recover and was therefore euthanized and excluded from the study.

The post challenge data for the period before euthanisation (at day 11) are indicated in Table 1. The average clinical scores, the survival time, the number of dead animals after challenge and the number of animals from which the pathogen could be re-isolated from the blood appeared to be improved for both vaccination schemes when compared to controls. The level of protection against the challenge with the serotype 9, ST16 strain appeared to comparable to that obtainable with an IgM protease against homologous challenge with a serotype 2 strain, as reported in WO2019/115741 and appeared to be markedly approved over the protection obtainable against serotype 9, ST16 as found in the '741 patent. This indicates that there is a synergistic effect between the two antigens. This effect seems to be more pronounced when they are combined in the unitary vaccine, in particular given the lower clinical scores and higher average survival time.

TABLE 1

| | Post challenge data | | | |
|---|---|---|---|---|
| Group | Clinical score | Survival time (days) | Dead after challenge | Positive blood isolation |
| 1 | 14 | 9.4 | 2/11 | 2/11 |
| 2 | 22 | 8.5 | 3/12 | 3/12 |
| 3 | 52 | 5.0 | 8/12 | 9/12 |

CONCLUSION

The present study design was more critical than the design as used in WO2019/115741. Thus, even if a comparable efficacy would be arrived at when using an alternative vaccine, this would already be an indication that the alternative vaccine is improved over the vaccines as described in WO2019/115741 (i.e. monovalent IgM protease or bacterin vaccines). However, it was found that with the novel combination vaccine, a markedly improved vaccine efficacy could be arrived at, indicating that the antigens have a synergistic interaction. This effect appeared to be higher when the antigens were combined in one single (unitary) formulation.

The invention claimed is:

1. A method for protecting pigs against a pathogenic infection with *Streptococcus suis* serotype 9, sequence type 16 comprising administering to a pig a combination of an IgM protease antigen of *Streptococcus suis* and a *Streptococcus suis* bacterin serotype 9, sequence type 16.

2. The method of claim 1, wherein the IgM protease antigen of *Streptococcus suis* and the *Streptococcus suis* bacterin are comprised in a single composition for administration to the pigs.

3. The method of claim 1, wherein the IgM protease antigen of *Streptococcus suis* is an IgM protease of *Streptococcus suis* serotype 2.

4. The method of claim 1, wherein the method comprises administering the IgM protease antigen of *Streptococcus suis* and the *Streptococcus suis* bacterin to the pigs at an age of at most 35 days.

5. The method of claim 1, wherein the method comprises administering the IgM protease antigen of *Streptococcus suis* and the *Streptococcus suis* bacterin before an age at which the pigs are weaned.

6. The method of claim 2, wherein the IgM protease antigen of *Streptococcus suis* is an IgM protease of *Streptococcus suis* serotype 2.

7. The method of claim 6, wherein the method comprises administering the IgM protease antigen of *Streptococcus suis* and the *Streptococcus suis* bacterin to the pigs at an age of at most 35 days.

8. The method of claim 3, wherein the method comprises administering the IgM protease antigen of *Streptococcus suis* and the *Streptococcus suis* bacterin to the pigs at an age of at most 35 days.

9. The method of claim 8, wherein the method comprises administering the IgM protease antigen of *Streptococcus suis* and the *Streptococcus suis* bacterin before an age at which the pigs are weaned.

10. The method of claim 7, wherein the method comprises administering the IgM protease antigen of *Streptococcus suis* and the *Streptococcus suis* bacterin before an age at which the pigs are weaned.

11. The method of claim 6, wherein the method comprises administering the IgM protease antigen of *Streptococcus suis* and the *Streptococcus suis* bacterin before an age at which the pigs are weaned.

12. The method of claim 4, wherein the method comprises administering the IgM protease antigen of *Streptococcus suis* and the *Streptococcus suis* bacterin before an age at which the pigs are weaned.

13. The method of claim 3, wherein the method comprises administering the IgM protease antigen of *Streptococcus suis* and the *Streptococcus suis* bacterin before an age at which the pigs are weaned.

14. The method of claim 2, wherein the method comprises administering the IgM protease antigen of *Streptococcus suis* and the *Streptococcus suis* bacterin before an age at which the pigs are weaned.

* * * * *